US012636284B2

(12) United States Patent
Barone et al.

(10) Patent No.: US 12,636,284 B2
(45) Date of Patent: May 26, 2026

(54) COMPOSITIONS FOR USE IN THE PREVENTION AND/OR TREATMENT OF INTELLECTUAL DISABILITY AND NEURODEGENERATIVE DISEASES IN A SUBJECT WITH DOWN SYNDROME

(71) Applicant: UNIVERSITA' DEGLI STUDI DI ROMA "LA SAPIENZA", Rome (IT)

(72) Inventors: Eugenio Barone, Rome (IT); Antonella Tramutola, Rome (IT); Marzia Perluigi, Rome (IT)

(73) Assignee: UNIVERSITA' DEGLI STUDI DI ROMA "LA SAPIENZA", Rome (IT)

( * ) Notice: Subject to any disclaimer, the term of this patent is extended or adjusted under 35 U.S.C. 154(b) by 384 days.

(21) Appl. No.: 18/560,142

(22) PCT Filed: Apr. 8, 2022

(86) PCT No.: PCT/IB2022/053323
§ 371 (c)(1),
(2) Date: Nov. 10, 2023

(87) PCT Pub. No.: WO2022/238779
PCT Pub. Date: Nov. 17, 2022

(65) Prior Publication Data
US 2024/0238286 A1     Jul. 18, 2024

(30) Foreign Application Priority Data

May 12, 2021    (IT) ........................ 102021000012173

(51) Int. Cl.
*A61K 31/4985*         (2006.01)
*A61P 25/28*           (2006.01)

(52) U.S. Cl.
CPC .......... *A61K 31/4985* (2013.01); *A61P 25/28* (2018.01)

(58) Field of Classification Search
CPC .................................................. A61K 31/4985
See application file for complete search history.

(56) References Cited

U.S. PATENT DOCUMENTS

2009/0017015 A1     1/2009   Hughes

OTHER PUBLICATIONS

International Search Report and Written Opinion of the ISA for PCT/IB2022/053323 mailed Jul. 15, 2022, 10 pages.

*Primary Examiner* — Golam M Shameem
(74) *Attorney, Agent, or Firm* — Nixon & Vanderhye, PC

(57) ABSTRACT

Composition for use in the prevention and/or in the treatment of intellectual disability and neurodegenerative diseases in a subject with Down syndrome, wherein the composition comprises as an active agent at least one compound belonging to the class of dipeptidyl-peptidase IV (DPP4) enzyme inhibitors and also to the class of gliptins.

9 Claims, 12 Drawing Sheets

| Subjects | PMI(hours) | Age(years) | Sex(M/F) | | Subjects | Age(years) | Sex(M/F) |
|---|---|---|---|---|---|---|---|
| Ctr G | 15.8 ± 3.0 | 21.3 ± 5.1 | 3/3 | | Ctr G | 6.5 ± 0.6 | 13/12 |
| DS | 16.0 ± 2.0 | 24.2 ± 5.9 | 5/3 | | DS | 8.3 ± 0.7 | 15/15 |
| DSAD | 5.76 ± 1.1 | 60.6 ± 1.2 | 4/4 | | | | |
| Ctr A | 14.6 ± 3.1 | 57.6. ± 2.5 | 6/2 | | | | |
| Ctr Eld | 3.89 ± 1.6 | 89.7 ± 1.5 | 4/4 | | | | |
| PCAD | 2.69 ± 0.15 | 86.3 ± 2.0 | 5/3 | | | | |
| MCI | 2.69 ± 0.14 | 89.6 ± 2.2 | 3/3 | | | | |
| AD | 2.69 ± 0.2 | 89.3 ± 1.4 | 4/4 | | | | |

COMPOSITIONS FOR USE IN THE PREVENTION AND/OR TREATMENT OF INTELLECTUAL DISABILITY AND NEURODEGENERATIVE DISEASES IN A SUBJECT WITH DOWN SYNDROME

CROSS-REFERENCE TO RELATED APPLICATIONS

This application is the U.S. national phase of International Application No. PCT/IB2022/053323 filed Apr. 8, 2022, which designated the U.S. and claims priority to IT 102021000012173 filed May 12, 2021, the entire contents of each of which are hereby incorporated by reference.

FIELD OF THE INVENTION

The present description refers to compositions for use in the prevention and/or treatment of intellectual disability and neurodegenerative diseases in a subject with Down syndrome.

BACKGROUND

Down syndrome (DS) is a condition caused by total or partial trisomy of chromosome 21, and is characterized by both physical and neurological defects, including mild to severe intellectual disability. In addition, individuals with DS have a high risk of developing neurodegenerative diseases, such as Alzheimer's disease (AD), usually starting at 40 years of age.

The recovery of the behavioral and neurophysiological deficit observed following the use of GABAA receptor (GABAA-R) inhibitors in mouse models of DS has led to the hypothesis that the intellectual deficit could depend on an imbalance in inhibitory circuits.

Most of the data produced so far in mouse models suggests that this imbalance may be attributable to a high number of inhibitory neurons and a higher frequency of inhibitory post-synaptic currents. At the same time, however, evidence to the contrary was also provided: in particular, the imbalance of the inhibitory circuits would cause an increase in the intracellular concentration of chlorine ions ($Cl^-$) in such a way that, following activation of the GABAA receptor, a flow of $Cl^-$ ions from the inside to the outside of the cell would be observed, with consequent depolarization of the neuron and reduced inhibition.

Consequently, although alteration of GABAergic transmission is the basis of cognitive retardation in subjects with DS, the causes of this alteration are still unclear and, to date, there are no therapeutic approaches useful for improving cognitive deficit and counteracting the development of neurodegenerative diseases in individuals with DS, particularly in adulthood.

Existing products such as GABA-A receptor antagonists or reverse inhibitors are not available in the clinic; when tested on humans they did not reach the primary and secondary endpoints and the study was stopped. Furthermore, the use of broad-spectrum GABAA receptor antagonists has not been approved as they can promote convulsions and anxiety crises.

SUMMARY OF THE INVENTION

The present description has the object of providing a composition that is efficient and safe for use in preventing and/or treating intellectual disability and neurodegenerative diseases in a subject with Down syndrome (DS).

According to the present description, this object is achieved thanks to the subject specifically indicated in the following claims, which are intended as an integral part of this description.

One embodiment of the present description provides a composition for use in the prevention and/or in the treatment of intellectual disability and neurodegenerative diseases in a subject with DS, wherein the composition comprises—as active agent—at least one compound belonging to the class of inhibitors of the enzyme dipeptidyl-peptidase IV (DPP4). The compound belonging to the class of DPP4 inhibitors also belongs to the class of gliptins, and may be selected in the group consisting of sitagliptin, vildagliptin, saxagliptin, linagliptin, gemigliptin, anagliptin, tenegliptin, alogliptin, trelagliptin, omarigliptin, evogliptin, glosogliptin, dutogliptin.

The present description also provides a method for treating intellectual disability and neurodegenerative diseases in a subject with DS, the method comprising the step of administering a composition to the subject comprising at least one compound belonging to the class of dipeptidyl-peptidase IV inhibitors (DPP4) as active agent.

The composition of the present description has been found to be effective not only in restoring GABAergic transmission and the cognitive deficit, but also in slowing the development of neurodegenerative diseases in subjects with DS, such as Alzheimer's disease, for example. Furthermore, the composition activates a specific molecular mechanism (described below), which in subjects with DS—unlike what has been demonstrated in healthy subjects—has been surprisingly able to promote neuroprotective (and non-neurotoxic) effects.

BRIEF DESCRIPTION OF THE FIGURES

One or more embodiments will be now described, purely by way of non-limiting example, with reference to the attached figures, wherein.

Figure 14:
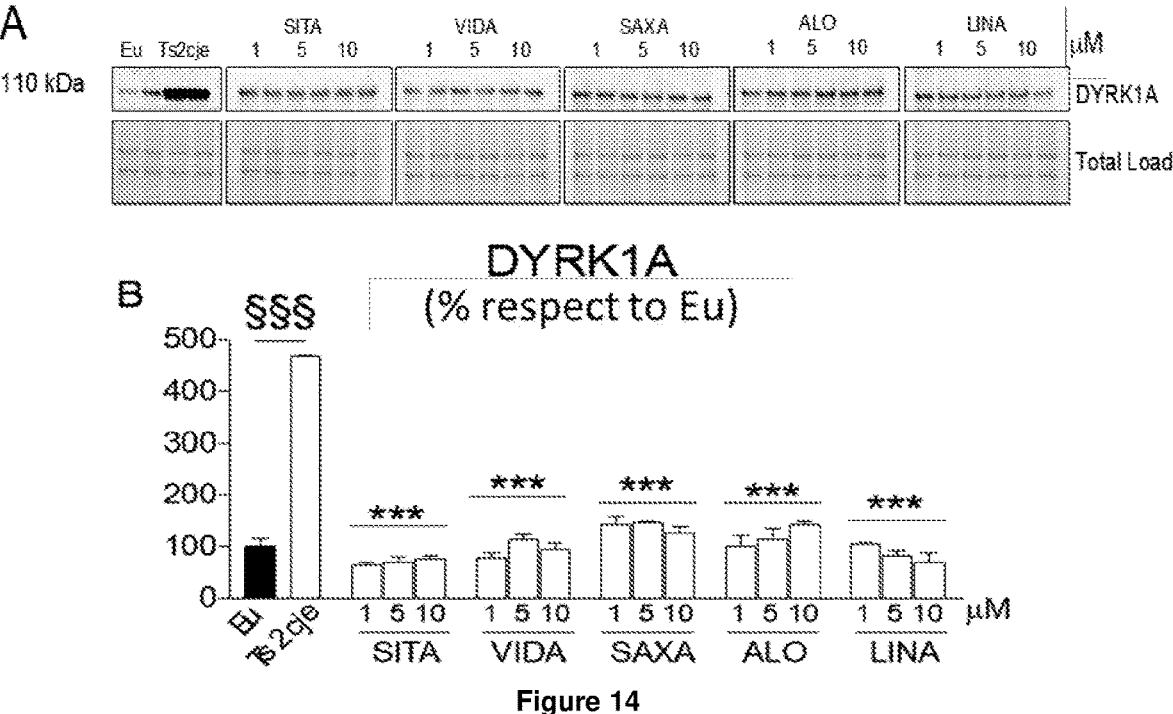
Figure 15:
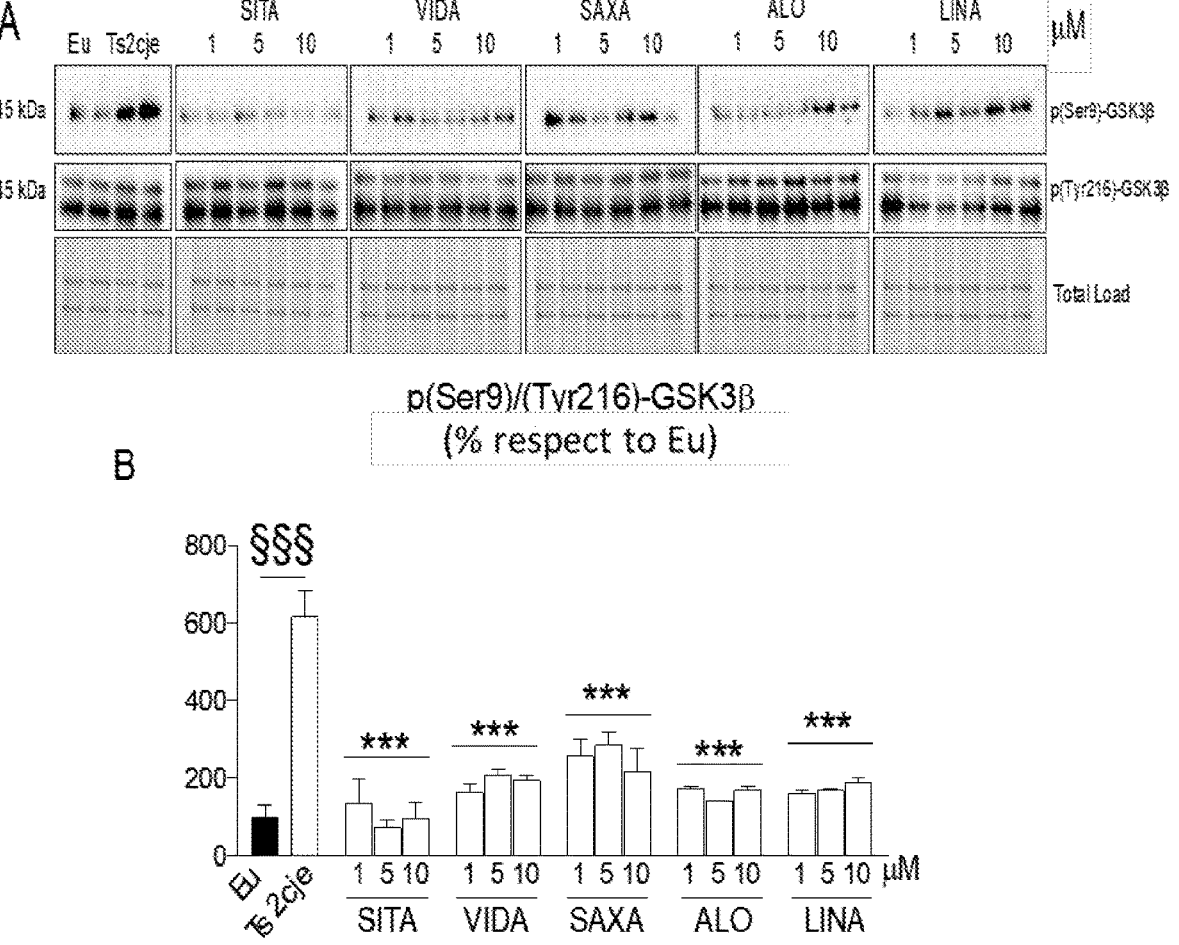

5 p<0.001 ANOVA analysis followed by Bonferroni corrected t test between Ts2cje vs Euploid groups; *** p<0.001 ANOVA analysis followed by Bonferroni corrected t-test between gliptin-treated vs untreated Ts2cje groups;

FIG. 14 shows the effects of gliptin administration on the total levels of the DYRK1A protein in hippocampal neurons isolated from Ts2cje mice. In (A) Representative image of the Western blot and of the electrophoretic run (gel-normalizer, total proteins) of the DYRK1A protein levels evaluated in neuronal cultures in response to treatment with different gliptins. In (B) the histograms report the densitometric analysis of the levels of DYRK1A, respectively, in the primary neurons isolated from euploid (Eu) and Ts2Cje mice, the latter treated with: Sitagliptin (SITA), Vidagliptin (VIDA), Saxagliptin (SAXA), Alogliptin (ALO) and Linagliptin (LINA), at three different doses (1 µM, 5 µM, 10 µM) for 24 hours. The reported densitometry values are expressed as a percentage of the Eu group. Data are presented as means±SEM of n=3 independent experiments per group. § § § p<0.001 ANOVA analysis followed by Bonferroni corrected t-test between Ts2cje vs Euploid groups; *** p<0.001 ANOVA analysis followed by Bonferroni corrected t-test between gliptin-treated vs untreated Ts2cje groups;

FIG. 15 shows the effects of gliptin administration on the activation of GSK3b protein in hippocampal neurons isolated from Ts2cje mice. In (A) Representative image of the Western blots and of the electrophoretic run (gel-normalizer, total proteins (Total load)) of the levels of activation of the GSK3b protein evaluated in neuronal cultures in response to treatment with different gliptins. In (B) the histograms report the densitometric analysis of GSK3b activation, represented as ratio between the inhibitory phosphorylation site (ser9) and the activating phosphorylation site (ty216), respectively, in primary neurons isolated from euploid (Eu) and Ts2Cje mice. Neurons isolated from Ts2cje mice were treated with: Sitagliptin (SITA), Vidagliptin (VIDA), Saxagliptin (SAXA), Alogliptin (ALO) and Linagliptin (LINA), at three different doses (1 µM, 5 µM, 10 µM) for 24 hours. The reported densitometry values are expressed as percentage of the Eu group. Data are presented as means±SEM of n=3 independent experiments per group. § § § p<0.001 ANOVA analysis followed by Bonferroni corrected t-test between Ts2cje vs Euploid groups; *** p<0.001 ANOVA analysis followed by Bonferroni corrected t-test between gliptin-treated vs untreated Ts2cje groups.

DETAILED DESCRIPTION OF PREFERRED EMBODIMENTS

In the following description, numerous specific details are provided to allow a thorough understanding of the embodiments. The embodiments may be implemented in practice without one or more of the specific details, or with other methods, components, materials, etc. In other cases, well-known structures, materials or operations are not shown or described in detail to avoid confuse certain aspects of the embodiments.

Reference throughout the present disclosure to "one embodiment" or "an embodiment" signifies that a particular aspect, structure or characteristic described with reference to the embodiment is included in at least one embodiment. Therefore, forms of the expressions "in one embodiment" or "in an embodiment" at various points throughout the present description are not necessarily all referring to the same embodiment. Moreover, particular aspects, structures or characteristics can be combined in any convenient way in one or more embodiments. The titles provided here are for convenience only and do not interpret the scope or purpose of the embodiments.

The alteration of the balance between excitatory and inhibitory activity of neuronal circuits is a factor responsible for intellectual disability as well as other neurological and psychiatric manifestations, which strongly affect the quality of life of people with DS and their families. In particular, there is an increased frequency of anxiety, clinically relevant sleep disturbances, and hyperactivity or movement disorders. Indeed, patients with DS demonstrate a higher incidence of epileptic episodes with the onset of seizures concentrated mainly during early childhood and aging. Dysfunctions of the GABAergic transmission pathway impair synaptic plasticity, learning and memory in people with DS by altering the balance between excitatory/inhibitory processes at the synaptic level.

As pointed out in the previous sections, however, there are currently no known drugs approved to treat or prevent cognitive impairment and the development of neurodegenerative diseases in individuals with DS.

The present description provides a composition for use in preventing and/or treating intellectual disability and neurodegenerative diseases in a subject with DS, wherein the composition comprises as active agent at least one compound belonging to the class of dipeptidyl-peptidase IV (DPP4) enzyme inhibitors and also to the class of gliptins. This compound may be selected in the group consisting of sitagliptin, vildagliptin, saxagliptin, linagliptin, gemigliptin, anagliptin, tenegliptin, alogliptin, trelagliptin, omarigliptin, evogliptin, glosogliptin, dutogliptin.

One advantage derived from the use of these compounds is that they have already been approved by various international regulatory agencies and some are already widely used in the treatment of other diseases; in particular, they represent drugs of choice for the treatment of type 2 diabetes mellitus and obesity.

All compounds belonging to the class of gliptins are able to inhibit the activity of the DPP4 enzyme and favor the consequent increase in the levels of incretins such as GLP1. These effects observed both in vitro and in vivo, promote an increase in insulin secretion and the reduction of glucagon secretion in a glucose-dependent manner, with consequent improvement of glucose uptake and homeostasis, as well as reduction of inflammatory processes, which are peculiar characteristics of metabolic diseases such as diabetes (both type 1 and type 2) and obesity (Incretins in the Therapy of Diabetic Kidney Disease. Przezak A, Bielka W, Pawlik A. Int J Mol Sci. (2021 Nov. 15; 22 (22): 12312. Doi: 10.3390/ijms222212312. PMID: 34830194). Furthermore, inhibitors of the DPP-4 enzyme do not have adverse effects on body weight or interact with other drugs. All gliptins have higher selectivity in comparison with the isoform 4 of the DPP4 enzyme with respect to other enzymes of the same family (DPP8 and DPP9). This is important since the enzymes DPP8 and DPP9 are involved in immune responses, and their eventual inhibition could cause immunological alterations.

As will be apparent from the following results, in vivo intranasal administration of sitagliptin ((R)-4-oxo-4-[3-(trifluoromethyl)-5,6-dihydro[1,2,4]triazole[4,3-a]pyrazin-7(8H)-yl]-1-(2,4,5-trifluorophenyl)butan-2-amine)), as a compound inhibitor of DPP4, has been found to be effective in restoring GABAergic transmission and intellectual disability in an animal model of DS. Furthermore, in the same model, the compound proved effective in slowing the development of neurodegenerative phenomena.

Intellectual disability is characterized by significantly below average intellectual functioning (often expressed as an IQ <70-75). Intellectual disability is considered a neurodevelopmental disorder. This condition appears in early childhood, usually before entering school. The age and onset characteristics depend on the etiology (cause) and severity of the impairment of the structure and/or brain functions. It is a disorder that includes both intellectual and adaptive functioning deficits in conceptual, social and practical areas, such as:

Deficits in intellectual functions, such as reasoning, problem solving, planning, abstract thinking, judgment skills, school learning and learning from experience, confirmed both by a clinical evaluation and by individualized and standardized intelligence tests;

Deficit in adaptive functioning that leads to failure to achieve developmental and socio-cultural standards of autonomy and social responsibility. Without constant support, adaptive deficits limit functioning in one or more activities of daily life, such as communication, social participation and autonomous life, across multiple environments such as home, school, work environment and community.

When intellectual disability is the expression of a particular genetic condition, e.g. DS, there may be a typical physical appearance.

In one or more embodiments, when the composition comprises sitagliptin as active agent, it may be contained in the composition in the form of a salt, preferably monohydrate phosphate salt 7-[(3R)-3-amino-1-oxo-4-(2,4,5trifluorophenyl)butyl]-5,6,7,8-tetrahydro-3-(trifluoromethyl)-1,2, 4 triazole[4,3-a]pyrazine phosphate (1:1) monohydrate.

The composition of the present description may comprise at least one compound belonging to the class of DPP4 inhibitors in a concentration comprised between 0.1 mM and 50 mM, preferably between 0.5 mM and 2.5 mM.

In one or more embodiments, the active agent may comprise, preferably may consist of, sitagliptin. In one or more embodiments, the composition may comprise at least one further compound as active agent.

In one or more embodiments, the composition of the present description is an intranasal composition, i.e. for an intranasal release.

The composition may be in the form of a unit dose to be administered once a day, wherein the compound belonging to the class of DPP4 inhibitors may preferably be present in an amount ranging from 0.001 mg to 1 mg.

As described below, the intranasal administration of the composition exerts a localized effect on the brain, without promoting significant effects at the peripheral level. A further advantage of this type of administration lies in the possibility of using a lower dosage of the active agent than for oral administration (OS); this is because the intranasal administration of the composition favors the crossing of the blood-brain barrier by the active agent. The total daily dose of the compound belonging to the class of DPP4 inhibitors, preferably sitagliptin, may range from 0.000015 mg/kg to 0.015 mg/kg body weight of the subject.

The intranasal administration is not invasive and is, therefore, easy to use even in subjects with DS. The composition may be administered in the form of a spray or aerosol. The composition may also be in the form of an aqueous solution.

The composition may further comprise at least one pharmaceutically acceptable excipient. The composition may also comprise at least one pharmaceutically acceptable vehicle known in the art selected, for example, from buffer solutions, physiological saline solution, water.

One of the advantages given by the composition of the present application lies in the use of at least one compound belonging to the class of DPP4 inhibitors as active agent, that is a class of compounds considered very safe due to the reduced number of side effects associated with their administration and already widely used in humans for treating diabetes and peripheral insulin resistance.

Administering a composition comprising these compounds is, therefore, a promising pharmacological alternative to the narrow range of compounds tested as antagonists of the neurotransmitter GABA in subjects with DS.

The Inventors of the present application have also shown that the effects of administering the composition are not limited to the correction of GABAergic transmission. The results described below clearly show a marked neuroprotective effect against the accumulation of neuropathological markers typical of AD.

The association between the neuroprotective effects affecting GABAergic transmission and those affecting the pathways normally altered and responsible for the development of AD represents an aspect never observed to date in the treatment of DS.

As will be described below, the Inventors have shown that sitagliptin, surprisingly, acts via a molecular mechanism expressed through the axis of the proteins DYRK1A and GSK3b. In particular, following the administration of the composition in a mouse model of DS, the Ts2Cje mouse, a reduction in the protein levels of DYRK1A and an increased activation of GSK3b, with consequent degradation of the gephyrin protein mediated by GSK3b and the restoration of the turnover of GABAA-R at the synaptic level was observed.

The final result caused a restoration of the correct GABAergic transmission, with a significant improvement in cognitive performance.

Similar results were obtained in vitro by administering sitagliptin, vildagliptin, saxagliptin, linagliptin, alogliptin to cell lines of primary cultures of neurons isolated from Ts2Cje mice.

Furthermore, the composition has been shown to be effective in increasing the levels of brain-derived neurotrophic factor (BDNF) and of the membrane proteins sintaxin-1 and PSD95 and—at the same time—in reducing the levels of beta-amyloid protein, of the phosphorylated Tau protein and oxidative stress in the brain of a mouse model of DS (Ts2Cje mice), thus helping to prevent and slow down neurodegeneration processes.

Figure 1:
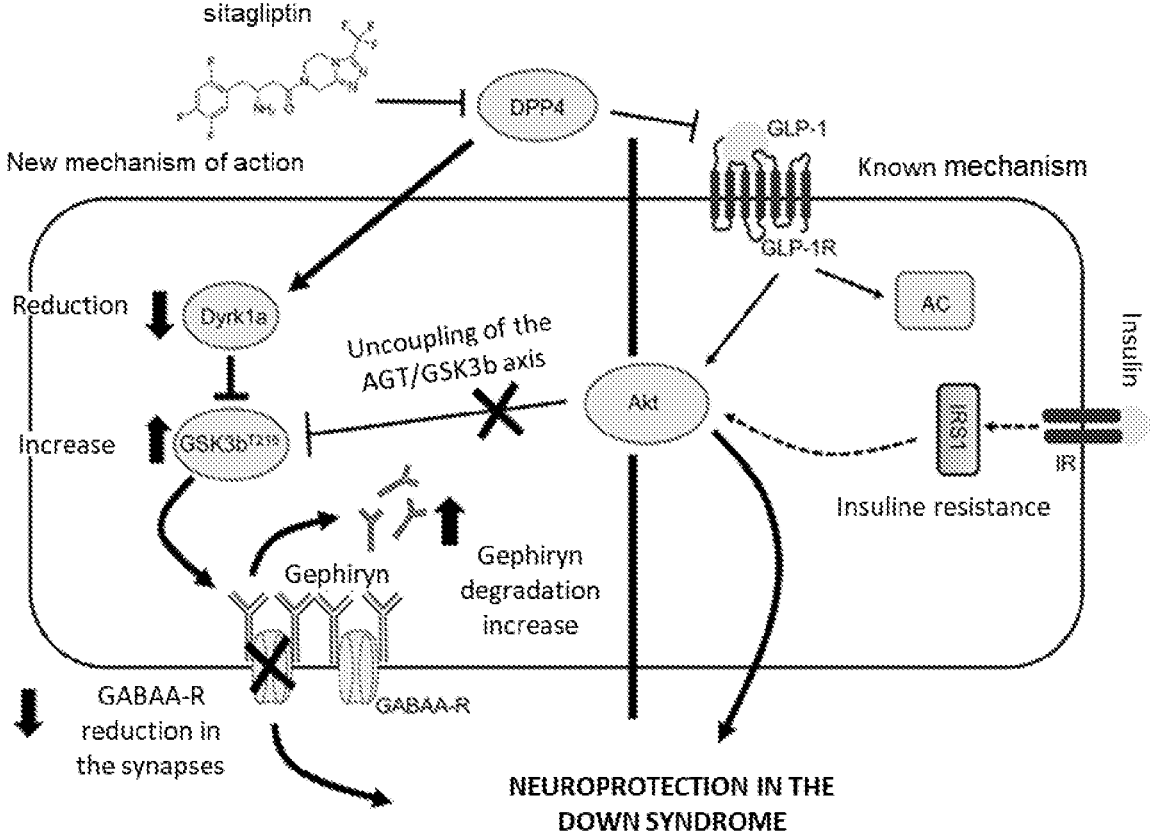
FIG. 1 shows a representative diagram of the molecular mechanism through which the neuroprotective effects of the administration of sitagliptin, as an inhibitor of the enzyme dipeptidyl-peptidase IV (DPP4), are expressed in a mouse model of DS; Arrow: activation; line: inhibition; thin dashed arrow: inhibition due to insulin resistance; arrow/thick line: effects relative to the new hypothesized mechanism of action of DPP4 on the DYRK1A/GSK3b/gephyrin axis in Ts2Cje mice; arrow/thin line, known mechanism of action for sitagliptin.

As illustrated in FIG. 1, under physiological conditions, the binding of glucagon-like peptide 1 (GLP1) to its receptor (GLP-1R) promotes activation of two main signaling pathways: the adenylate cyclase (AC) pathway and the phosphatidylinositol 3-kinase/protein kinase B (PI3K/Akt) pathway, which mediate the insulinotropic and neurotrophic effects associated with GLP1. The PI3K/Akt pathway is shared with the insulin signal. In fact, following binding of insulin to its receptor (IR), phosphorylation and consequent activation of the substrate of the type 1 insulin receptor (IRS1) is observed, which—in turn—mediates activation of the PI3K/Akt pathway. In conditions of insulin resistance, the IRS1 protein is inhibited, so activation of the downstream PI3K/Akt pathway does not occur. For this reason, the use of drugs that promote an increase in GLP1 concentrations or GLP-1R agonists are used to bypass IRS1 inhibition and restore activation of the PI3K/Akt pathway. GLP1 has a fairly short half-life as it is inactivated by the enzyme dipeptidyl-peptidase type 4 (DPP4) through a proteolytic cut that leads to the elimination of two amino acids at the level of the N-terminal portion of the protein, thus transforming GLP1-9-36 (active form) into GLP1-7-36 (inactive form). Compounds belonging to the class of DPP4 inhibitors, sitagliptin, for example, are able to increase the extracellular concentration of GLP1 and thus promote its insulinotropic effects. This mechanism was known to the Inventors of this application, whose goal was initially to restore activation of the insulin signal in subjects with DS.

Surprisingly, however, the Inventors observed a new, never-before-described molecular mechanism underlying the neuroprotective effects of sitagliptin in Ts2Cje mice. DS is characterized by the triplication of chromosome 21, on which the gene encoding the dual specificity tyrosine phosphorylation regulated kinase 1A (DYRK1A) protein is located. This protein is over-expressed both in humans with DS and in mouse models for DS, and its over-expression is responsible for numerous neurotoxic effects. Furthermore, DYRK1A promotes inhibition of the glycogen synthase kinase 3 beta (GSK3b) protein. Among the many effects mediated by GSK3b, the one involving the turnover of the GABAergic receptor type A (GABAA-R) appears to be entirely relevant for the purposes of the invention described here. In fact, normally, GSK3b promotes phosphorylation and consequent degradation of the gephyrin protein, which anchors GABAA-R at the post-synaptic membrane level. Consequently, over-expression of DYRK1A in DS is responsible for over-inhibition of GSK3b and the consequent accumulation of GABAA-R at the post-synaptic level. This would be one of the reasons responsible for the dysfunction of GABAergic transmission in DS.

Treatment with a compound belonging to the class of DPP4 inhibitors has been shown to be able to promote reduction of DYRK1A levels and favor restoration of GSK3b activation with consequent degradation of gephyrin. In this way, restoration of the normal turnover of GABAergic receptors is assisted at the post-synaptic level with positive effects on the mechanisms underlying synaptic plasticity in subjects with DS.

The restoration of GABAergic transmission and, therefore, improvement of the cognitive deficit in DS is effectively achieved through a completely new molecular mechanism.

Almost all of the studies in the literature show how prolonged and excessive activation of the GSK3b protein is associated with the development of neurodegeneration, during the normal aging process, in AD and in the development of epilepsy. Molecules proposed as GSK3b inhibitors are consequently numerous. On the contrary, activation of the GSK3b protein in the brain of Ts2Cje mice has been proved a key event in order to restore GABAergic transmission and, therefore, to improve the cognitive deficit in subjects with DS.

The results described below also highlight how GSK3b activation in the brain of Ts2Cje mice is not associated with the accumulation of typical AD markers such as phosphorylated Tau protein or beta-amyloid (Ab), suggesting that GSK3b activation following administration of a compound belonging to the class of DPP4 inhibitors, such as sitagliptin, follows different signal transduction pathways in DS.

Materials and Methods

Cerebral Cortex Samples

Human brain frontal cortex samples were obtained from the University of California Alzheimer's Disease Research Center (UCI-ADRC) and the University of Kentucky Alzheimer's disease Center. Table 1 shows the characteristics and demographics of the cases included in the study. The cases of DS were divided into two groups, with (DSAD, n=8) or without (DS, n=8) a neuropathological diagnosis for AD. The age of DS cases is less than 40 years, while DSAD cases are older than 40 years. For this reason, the controls were divided into two groups: young controls (Ctr G, n=6), to be compared with the DS group, having an age≤45 years; elderly controls (Ctr A, n=8), to be compared with DSAD since they are over 45 years old. The plasma samples of DS patients (n=30) and the respective controls (Ctr y, n=25), used to evaluate the enzymatic activity of DPP4, were collected at the Bambino Gesù pediatric hospital.

As for the cortex samples of AD patients, they were obtained by considering the three different stages of the disease (Preclinical AD, PCAD (n=8); Mild Cognitive impairment, MCI (n=6) and overt AD, AD (n=8)). Elderly controls (Ctr Eld, n=8) were selected on the basis of age in order to be able to compare them to cases with AD. All results obtained from human autopsy samples were analyzed considering the difference in the post-mortem interval (PMI) between groups.

Regarding the post-mortem samples, informed consent was not required since they are autopsy samples stored in the UCI-ADRC and University of Kentucky bio-banks. As for the plasma samples obtained from the Bambino Gesù Pediatric Hospital, their collection was approved by the Ethics Committee of the same hospital with protocol no. 1771_OPBG_2019.

Murine Samples and Treatment

Ts2Cje mice (Rb-12.Ts171665Dn2Cje) are a well-established animal model for the study of DS, they are trisomic for chromosome 16 (Mmu16), from Mrp139 to the distal telomere, which is a homologue of human chromosome 21 (hsa21). The first generations of parents of trisomic and non-trisomic mice were purchased from Jackson Laboratories (Bar Harbor, ME, USA). The murine colony is maintained by crossing the Ts2Cje trisomic females with F1 hybrid males (B6EiC3SnF1/J), from the subsequent crossing we obtain litters for 40% trisomic (Ts2Cje), while the remaining 60% of the newborns are euploid (Eu). Offspring trisomy is confirmed using standard PCR, validated by Reinholdt et al. The mouse colony was housed in the enclosure of the Department of Histology of the Sapienza University of Rome. Environmental conditions of the enclosure remained constant and monitored (temperature 22±2° C., lighting from 7:00 to 19:00 and constant humidity 50-60%), with food and water ad libitum. All experiments were conducted in strict compliance with the Italian National Laws (DL 116/92) and the Directives of the Council of the European Communities (86/609/EEC). Furthermore, the experimental protocol adopted for the studies on Ts2Cje was approved by the Ministry of Health (#1183/2016-PR). In the study, every effort was made to minimize the number of animals used and their suffering.

For evaluating age-dependent changes in the enzymatic activity of DPP4 (described below) in the hippocampus, the euploid and Ts2Cje mice were sacrificed at different ages 1-3-9-12 months (n=6 per group). This experiment allowed us to identify a specific age in which the enzymatic activity of DPP4 increased in trisomic mice (9 months) compared to euploids. This age was chosen for treatment with the compounds object of the study.

The mice, at the age of 9 months, were divided into four experimental groups: vehicle-treated euploids (Eu vehicle, n=10), vehicle-treated Ts2Cje (Ts2 vehicle, n=10), sitagliptin-treated euploids (Eu sitagliptin, n=10) and Ts2Cje treated with sitagliptin (Ts2 sitagliptin, n=10). Administration was intranasal and each mouse received, daily, 10 μL of vehicle (physiological saline solution) or sitagliptin dissolved in physiological saline solution (Selleckchem #S4002, 5 mM) in the nostril for 21 days. For the duration of the treatment, the mice were weighed weekly in order to assess any weight changes. After 21 days of treatment, the animals underwent a behavioral test to assess their memory and learning abilities. After the behavioral test, metabolic parameters such as blood glucose (both fasting and under the glycemic curve), body surface area (BSA) and body mass index (BMI) were assessed. Finally, animals were sacrificed using cervical dislocation. The brain and peripheral areas were isolated and collected in liquid nitrogen and subsequently stored at –80° C. until they were used for biochemical analyzes.

Metabolic Parameters

The body weight of the animals (gr) of the four experimental groups (Eu vehicle, Eu sitagliptin, Ts2 vehicle and Ts2 sitagliptin) was monitored once a week from the start of treatment (0-7-14-21 days). Furthermore, mice were measured at the beginning and at the end of the treatment to evaluate the length in centimeters (cm). For calculating the body mass surface, the DuBois equation was used: body surface area (m$^2$)=0.007184×weight (0.425 kg)×height (0.725 cm). The body mass index was calculated as the ratio between weight and BSA (gr/m$^2$). At the end of the treatment, the glucose tolerance test (GTT) was carried out on the four experimental groups. After a fasting period of 6 hours, the animals' basal blood glucose was assessed with a small blood sample from the tail (T0). Subsequently, the same animals were treated with a glucose solution (10%, intraperitoneal injection) and blood glucose was measured with a glucometer (lineD ORO, Bioseven) after 30-60-90-120 minutes.

Cognitive Test

The Novel object recognition (NOR) test is a relatively fast and efficient means of testing different stages of learning and memory in mice. The test is based on a minimum of three sessions: a habituation session (Day 1), a training session (Day 2) and a test session (Day 3). Training simply involves visual exploration of two identical objects, while the test session involves replacing one of the previously explored objects with a new object. Since rodents have an innate preference for novelty, a rodent that remembers the familiar object will spend more time exploring the new object. The mice belonging to the four experimental groups (Eu vehicle, Eu sitagliptin, Ts2 vehicle and Ts2 sitagliptin) were subjected to the following cognitive test.

In the habituation stage, each animal can freely explore the arena for 10 minutes (50 cm deep×30 cm wide×30 cm high) in the absence of objects. During the training stage, a single animal is placed in the arena containing two identical objects (two balls) for 10 min. In the testing stage, after 24 hours, the animal is brought back to the arena with two objects, one is the familiar object and the other is a new object (ball+lego). The experimental context does not change during the 3 days of testing. In the analysis stage, the discrimination index (DI) and preference index (PI) are evaluated. The discrimination index (DI) allows calculation of the animal's ability to discriminate between new (TN) and familiar (TF) objects [DI=(TN–TF)/(TN+TF)]. While, the index of preference (PI) is the ratio between the amount of time spent exploring both objects in the training stage (A, B) or the new object in the testing stage (C) compared to the total time spent in the exploration of both objects in percentage i.e. A, B or C/(A+B+C)×100(%). Therefore, a preference index above 50% indicates a clear preference for the new object.

Electrophysiology

The brain sections containing the hippocampus were obtained from mice belonging to the four experimental groups (Eu Veh, Eu SITA, Ts2 Veh and Ts2 SITA) at 9 months of age after being euthanized by an overdose of isofluorane. Brains were quickly removed and placed in an ice-cold cutting solution containing the following (in mM): 124 NaCl, 3.2 KCl, 1 NaH$_2$PO$_4$, 2 MgCl$_2$, 1 CaCl$_2$), 26 NaHCO$_3$, 10 glucose, 2 Na-pyruvate and 0.6 ascorbic acid, pH 7.4, 95% O$_2$/5% CO$_2$. The brain sections containing the hippocampus (300 mm thick) were cut using a vibratome (VT1000S; Leica Microsystems) and immediately transferred to an incubation chamber filled with ACSF containing the following (in mM): 124 NaCl, 3.2 KCl, 1 NaH$_2$PO$_4$, 1 MgCl$_2$, 2 CaCl$_2$, 26 NaHCO$_3$ and 10 glucose, pH 7.4, 95% O$_2$/5% CO$_2$. Brain sections were allowed to recover at 32° C. for 1 hour before being equilibrated to room temperature.

For electrophysiological recordings, brain sections were transferred to a recording chamber constantly perfused with heated ACSF (32° C.) and bubbled with 95% O$_2$/5% CO$_2$. Subsequently, the slices were used for electrophysiological recordings. All electrophysiological recordings were performed using the patch-clamp technique in the whole-cell configuration. Recordings were obtained with an Axopatch 700B amplifier (Molecular Devices) and the stimulation and acquisition of the data were performed with a Digidata 1200 and with the pCLAMP 11 software (Molecular Devices). Spontaneous neurotransmitter release was investigated with voltage-clamp experiments. The obtained borosilicate glass (Warner Instruments, Inc) recording pipettes with a resistance of 3-5 MΩ were fabricated using a Narishige PC-10 puller (Japan) and filled with an inner solution containing (in mM): 146 K-gluconate, 18 HEPES, 1 EGTA, 4.6 MgCl$_2$, 4 NaATP, 0.3 Na2GTP, 15 creatine phosphate. Neurons were maintained at –70 mV holding potential.

Membrane capacity and resistance were assessed in the same neurons. The resting membrane potential was studied by means of current-clamp experiments.

Preparation of the Samples

Total protein extracts were prepared from the frontal cortex for human autopsy samples and from the hippocampus for mouse samples, using RIPA solution (pH 7.4) containing TrisHCl (50 mM, pH 7.4), NaCl (150 mM), 1% NP-40, 0.25% sodium deoxycholate, ethylenediamine tetracetic acid (EDTA) (1 mM), and 0.1% sodium dodecyl sulfate (SDS). For studying DPP4 enzymatic activity, samples were used without inhibitors of proteases and phosphatases, which otherwise would have also inhibited the activity of DPP4 itself. For the rest of the experiments, protein extracts were supplemented with cocktails of protease and phosphatase inhibitors (Sigma Aldrich, St Louis, MO, USA). Brain tissues were homogenized in the solution described above by sonication, and centrifuged at 14,000 rpm for 30 min at 4° C. The supernatant was used to determine total protein concentration by means of the bicinchoninic acid assay (BCA, Pierce, Rockford, IL).

Dosage of the Enzymatic Activity of DPP4

The enzymatic activity of DPP4 was measured according to the assay by Matheeussen et al., which measures the rate of cleavage of 7-amino-4-methylcoumarin (AMC) from the synthetic substrate H-glycyl-prolyl-AMC (H-Gly-Pro-AMC; BioVi-sion, San Francisco, California, USA, nmol/min/ml). In order to attribute the measurement of enzyme activity exclusively to DPP4 and not to other members of the DPP family, a parallel set of samples was incubated with the selective DPP4 inhibitor, sitagliptin, at a final concentration of 500 μM. For each sample, the DPP4 activity was then calculated based on the residual fluorescence obtained by subtracting the fluorescence of the sample treated with the inhibitor from that of the sample without inhibitor.

Immunofluorescence

Immunofluorescence was performed on the brains of euploid and Ts2Cje mice treated with vehicle, and the Ts2Cje group treated with sitagliptin. Brains were placed in 4% paraformaldehyde for 24 hours. Brains were then fixed over the subsequent 48 hours in a 20% sucrose solution. Brain sections were then cut to a thickness of 15 μm using a cryostat (Leica System) and stored in an aqueous solution of PBS containing 0.02% $NaN_3$ at 4° C. until use. Slices thus obtained were mounted on slides and were blocked and permeabilized by blocking solution (10% of normal goat serum and 0.2% Triton X-100 in TBS) for 2 hours. Subsequently, sections were incubated overnight at 4° C. with the following antibodies: GABA receptor α2 (1:500, Synaptic System, #224-103) and gephyrin (1:250, Synaptic System, #147-111), p-Tau Ser404 (1:500, Abcam, #92676), sintaxin-1 (1:250, Genetex, #GTX113559) and PSD95 (1:250, Abcam, #ab18258), BDNF (1:200, Santa Cruz, sc-546).

The following day, the same slices were incubated with a mix of fluorescent secondary antibodies, to evaluate the co-localization of the two proteins, anti-mouse Alexa Fluor 488 nm for gephyrin and anti-rabbit Alexa Fluor 594 nm for GABA α2 (1:1500, Invitrogen, Carlsbad, California, CA, USA) for 2 hours at room temperature. The slices were then washed again and incubated with DAPI nuclear marker (1:10000, Invitrogen, Carlsbad, California, CA, USA). To subtract the non-specific background signal created by the secondary antibody, some sections were incubated only with the secondary antibody. Finally, the sample was sealed with a cover slip via fluorimount (Sigma-Aldrich, St Louis, MO, USA). The acquisition and analysis of brain sections was carried out using Leica TCS SP5x confocal microscopy and ImageJ analysis software.

Western Blot

For Western blots, 20 μg of proteins from the hippocampus of mice belonging to the four experimental groups were separated by 4-15% SDS-PAGE Criterion™ TGX (Tris-Glyicine eXtended) Stain-Free™ (Bio-rad, Hercules, CAUSE). This type of gel allows a rapid acquisition of the protein run in the ultraviolet (UV) by Chemidoc™ MP imaging systems (Bio-rad, Hercules, CA, USA). Therefore, the gel, once the image has been acquired, represents the total of the loaded proteins (Total Load), which will then be used to normalize the specific proteins to be examined. After electrophoresis and gel imaging, proteins are transferred via the semi-dry TransBlot Turbo apparatus (Bio-Rad Laboratories) onto nitrocellulose membranes (Bio-Rad, Hercules, CA, USA). Nitrocellulose membranes are blocked with 3% bovine serum albumin (BSA) in a solution of Tween 20-TBS and incubated overnight at 4° C. using specific primary antibodies: p(T216)-GSK3B (1:1000, Santa Cruz, #sc-135653), p(S9)-GSK3β (1:1000, Cell Signaling, #5558S), GSK3β (1:1000 Abcam, #93926) and DYRK1A (1:1000, Cell Signaling, #8765S), MAPK44/42 (1:1000, Cell Signaling, #9102), p(Thr202/Tyr204)-MAPK44/42 (1 1000, Cell Signaling, #9101), Akt (1:2000, Bio-Rad, # vma00253K), p(S473) Akt (1:1000, Cell Signaling, #4060S). After three washes with a T-TBS buffer solution, membranes were incubated for 1 hour at room temperature with the secondary antibodies. Secondary antibodies with peroxidase activity are anti-mouse or anti-rabbit (1:5000, Bio-rad, Hercules, CA, USA). Membranes were developed using Clarity Enhanced Chemiluminescence (ECL), a chemiluminescent substrate (Bio-rad, Hercules, CA, USA) and acquired with Chemidoc Mp (Bio-rad, Hercules, CA, USA). Finally, the results obtained were analyzed using the ImageLab program (Bio-rad, Hercules, CA, USA).

Slot Blot

For analyzing total levels of modified proteins for 4-hydroxynonenal (4-HNE) and for 3-nitrotyrosine (3-NT) in Euploid and Ts2Cje mice treated with vehicle and sitagliptin, respectively, 5 μl of homogenated sample, as described in paragraph "sample preparation", was incubated with 10 μl of Laemmli buffer containing: Tris HCl 0.125M pH 6.8, 4% (w/v) of SDS and 20% (v/v) of glycerol. The samples (250 μl per well) were loaded into the wells of the slot-blot apparatus and transferred to a nitrocellulose membrane. The membrane was blocked for 2 h with a 3% solution of bovine serum albumin in T-TBS, and incubated with a primary anti-HNE polyclonal antibody (1:3000; HNE, NOVUS, #NB100-63093) or anti-3-NT (1:1000; Sigma Aldrich, #SAB52000009), for 2 hours at room temperature. The membrane was washed with T-TBS and incubated with alkaline phosphatase conjugated anti-rabbit or anti-mouse secondary antibody (1:5000, Sigma Aldrich) for 1 hour at room temperature. Membranes were acquired with Chemidoc Mp (Bio-rad, Hercules, CA, USA). Finally, the results obtained were analyzed using the ImageLab program (Bio-rad, Hercules, CA, USA).

ELISA Aβ 1-42

The Aβ1-42 ELISA kit (KMB3441; Invitrogen Thermo Fisher Scientific) was used to determine β-amyloid peptide 1-42 levels in Eu and Ts2Cje mice treated with vehicle and sitagliptin, respectively (n=6/group). The 3x-Tg mouse, an animal model commonly used for the study of Alzheimer's disease (n=2/group), was used as a positive control for the production of β-amyloid 1-42. Briefly, ~10 mg of hippocampus was homogenized in DEA buffer (10 μL/mg tissue; 0.2% diethanolamine and 50 mM NaCl) to which the protease inhibitor cocktail (1:100; Millipore) was added. The sample was centrifuged at 15,000 rpm for 1 hour 30 min at 4° C., the supernatant was stored for measuring ß-amyloid 1-42 following the instructions given by the kit manufacturer. The calculations for the quantization of β-amyloid were carried out using GraphPad Prism 8.0 software (GraphPad, La Jolla, CA, USA).

In Vitro Test

Sitagliptin, vildagliptin, saxagliptin, linagliptin, and alogliptin were administered to primary cultures of hippocampal neurons isolated from Ts2Cje and euploid mice at day 0-1 from birth.

In order to isolate primary hippocampal neurons, hippocampi from Ts and euploid mice were mechanically dissociated in PBS (with $Ca^{2+}$ and $Mg^{2-}$) and centrifuged (3 minutes, 1100 rpm, 25° C.). Subsequently, the pellet was resuspended in 0.25% trypsin solution and centrifuged further for 3 minutes at 1100 rpm at $T_{amb}$. At this point, the cell extract was resuspended in MEM 1 culture medium (Minimum Essential Medium complemented with fetal bovine serum (FBS-1%), L-glutamine 200 mM (1%), glucose 25 mM (1%), gentamicin 0.1 mg/ml) and centrifuged for 10 minutes, 1100 rpm at 25° C. The resulting pellet was resuspended in a second culture medium, MEM2 (Minimum Essential Medium complemented with FBS (5%), human serum (5%), 200 mM L-glutamine (1%), 25 mM glucose (1%), gentamicin 0.1 mg/ml) and cells were plated in wells (300,000 cells/well) previously treated with poly-D-Lysine. After 24 hours, the culture medium was replaced with Neurobasal 1 (Neurobasal Medium complemented with B27 (2%), L-glutamine 200 mM (1%), gentamicin 0.1 mg/ml), to promote neuronal differentiation. After 4 days, the culture medium was again replaced with Neurobasal 4 (Neurobasal Medium complemented with B27 (2%), gentamicin 0.1 mg/ml). After 6 days, Ts neurons were treated with 3 doses (1, 5, 10 μM) of sitagliptin (SITA), vildagliptin (VIDA), saxagliptin (SAXA), alogliptin (ALO) and linagliptin (LINA) for 24 hours. At the end of the treatment, protein extracts were used to evaluate DPP-IV enzymatic activity, levels of the DYRK1A protein and activation of the GSK3b protein, with the methods described above.

Statistical Analysis

All statistical analyzes were performed using GraphPad Prism 8.0 software. The analysis of variance (One way-ANOVA) was used to compare the obtained results accompanied by the Bonferroni post-hoc test for multiple comparisons. Values of p<0.05* were considered statistically significant.

Results

Figure 2:
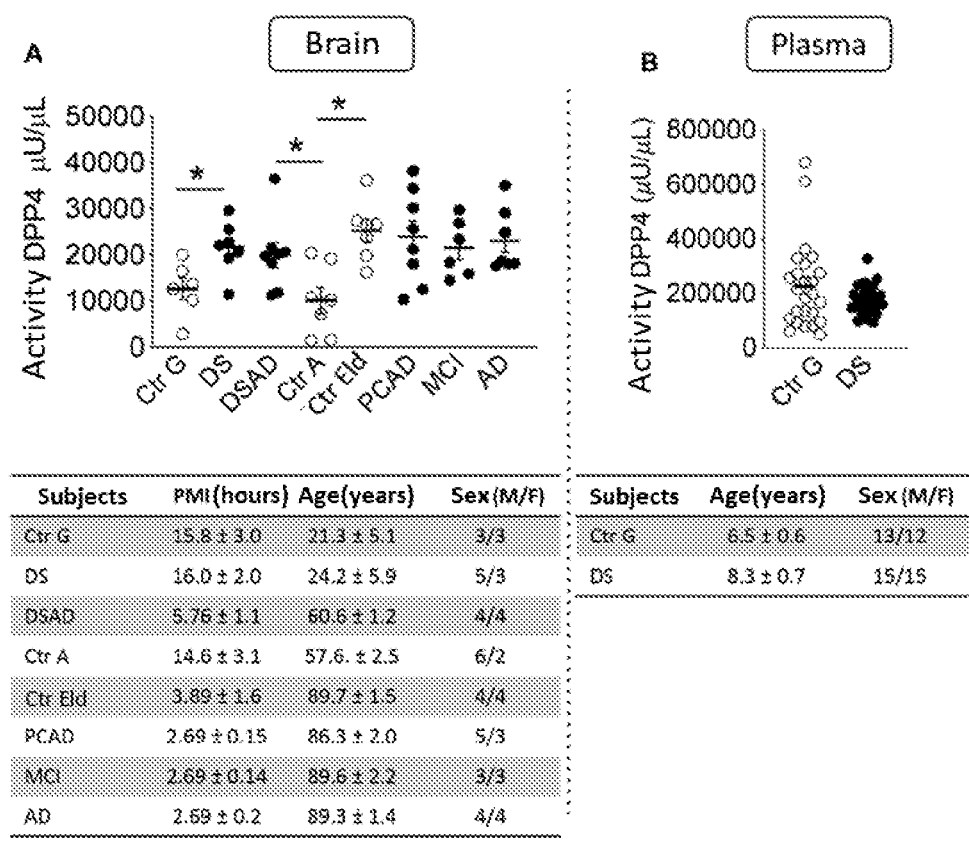
FIG. 2 shows the analysis of the activity of the DPP4 enzyme in human samples. In (A) analysis of DPP4 activity in (i) post-mortem samples of the prefrontal cortex isolated from individuals with DS before (<40 years) and after AD development (>40 years) and (ii) post-mortem samples of the inferior parietal lobule isolated from AD patients at different stages of the disease. The Table shows the characteristics of the samples analyzed. Ctr G: young controls of less than 40 years of age; DS: people with DS under 40 years of age; DSAD: people with DS who have developed AD and over the age of 40; Ctr A: adult controls over the age of 40; Ctr Eld: elderly controls relative to subjects with AD and over 80 years of age; PCAD (pre-clinical AD): subjects affected by AD but in a pre-clinical stage of the disease; MCI (amnestic mild cognitive impairment): subjects affected by AD but in an intermediate stage of the disease; AD: subjects with full-blown AD. PMI (post-mortem interval): time interval between death and brain removal; Age: age expressed in years; Sex: sex of the subjects included in the study. In (B) analysis of DPP4 activity in plasma samples taken from people with DS and relative controls. *, p<0.05 ANOVA analysis followed by Bonferroni corrected t-test.

As illustrated in FIG. 2, the analysis of the DPP4 enzyme activity, evaluated in post-mortem samples of the prefrontal cortex isolated from people with DS both before and after the development of Alzheimer's disease (DSAD), compared with the respective controls, shows a significant increase in people with DS (FIG. 2A). The same increase is not observed in plasma samples collected from people with DS and related controls (FIG. 2B), suggesting a particularly significant alteration in the brain. Furthermore, the same evaluation conducted in post-mortem samples of the brain (inferior parietal lobule) isolated from patients with AD at different stages of the disease and related controls, provides evidence of how the increase in DPP4 activity is an alteration mainly associated with age rather than AD pathology (FIG. 2A).

These results are in agreement with the prevailing hypothesis in the literature that refers to DS as a condition that promotes an accelerated aging process.

Figure 3:
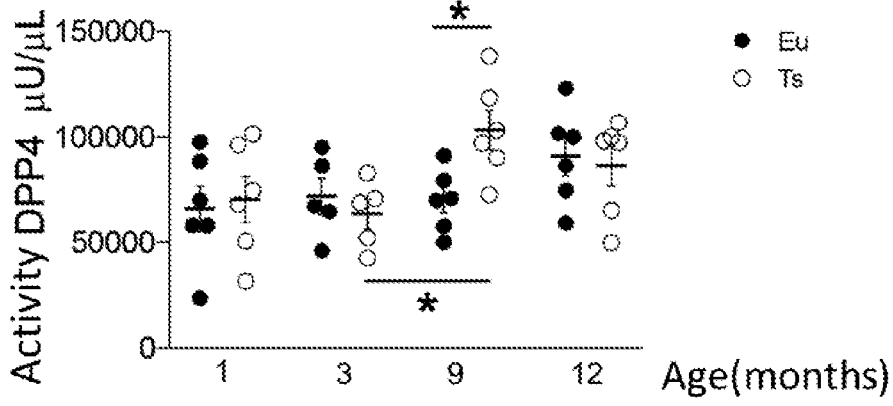
FIG. 3 illustrates the analysis of DPP4 enzyme activity in hippocampal samples isolated from Ts2Cje mice at different ages. Eu: control euploid mice; Ts: Ts2Cje mice. *, p<0.05 ANOVA analysis followed by Bonferroni corrected t-test.

Furthermore, analysis of DPP4 enzyme activity in prefrontal cortex samples isolated from the Ts2Cje mouse (a mouse model of DS) shows an age-dependent increase congruent with the results obtained in humans (FIG. 3), and supports the use of this animal model for subsequent studies. In particular, the effects of administration of the composition were evaluated in Ts2Cje mice at 9 months of age, as this was the age associated with a significant increase in the activity of DPP4 in the brain.

Identifying a new molecular modulation mechanism mediated by sitagliptin, as a compound inhibitor of DPP4, allowed demonstration of its efficacy in promoting restoration of GABAergic transmission in Ts2Cje mice, which is associated with a significant improvement in cognitive deficit. The treatment also promotes a marked improvement of the neuropathological picture.

Figure 4:
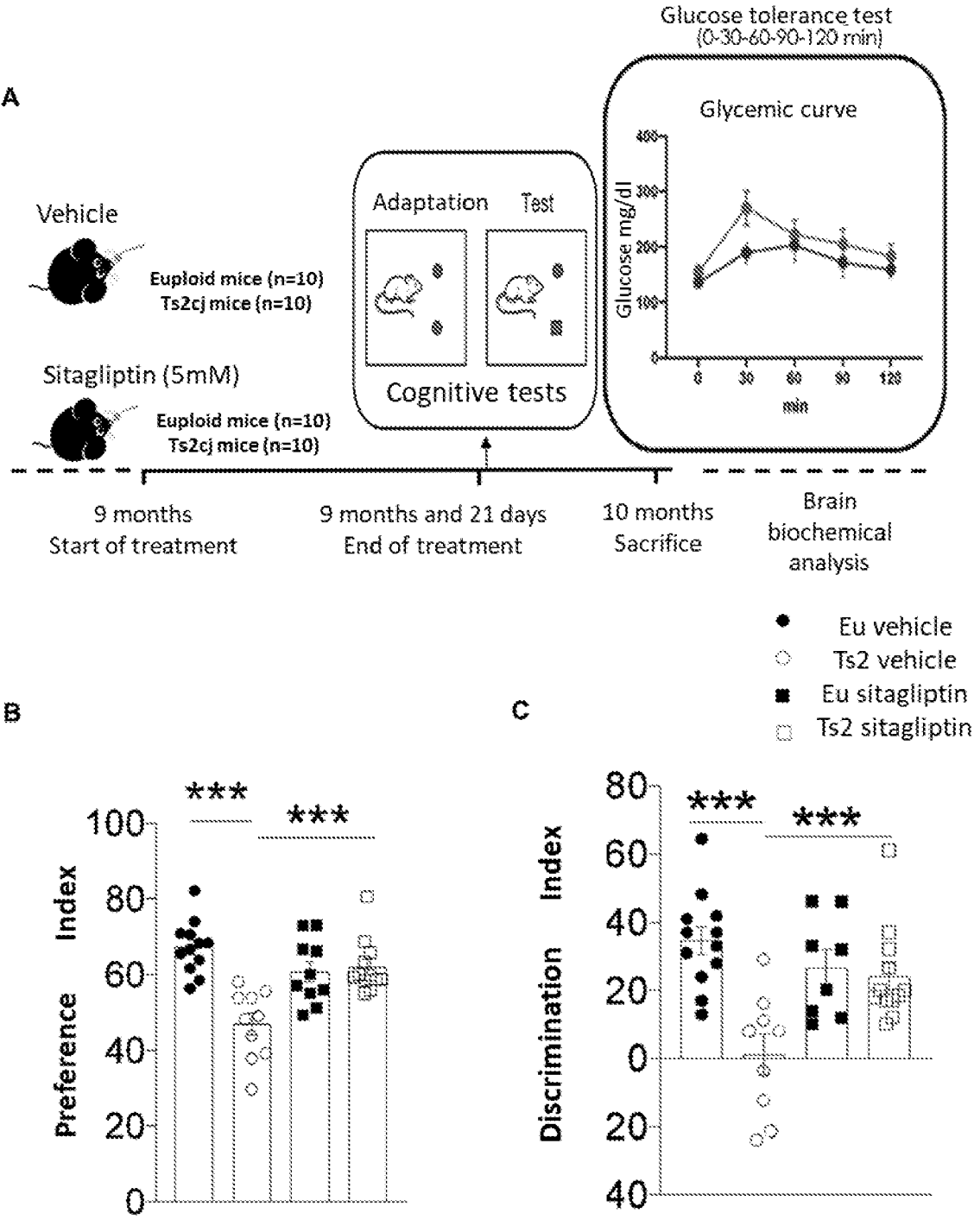
FIG. 4 concerns with the effects of sitagliptin administration on memory. In (A) the experimental plan is described. At the end of the treatment, the animals of the four experimental groups were subjected to a behavioral test for evaluating long-term memory. The index of preference (B) and the index of discrimination (C) of rodents measured, respectively, in euploid and Ts2Cje animals treated with sitagliptin or with vehicle (saline solution) are reported. *, p<0.05, ANOVA analysis followed by Bonferroni corrected t-test.

In particular, administering the composition comprising sitagliptin (5 mM) intra-nasally (10 μL/nostril, once a day for 21 days) promotes a marked improvement in cognitive performance, evaluated through a standard test, the novel object recognition (NOR), in Ts2Cje mice at 9 months of age (FIG. 4).

Figure 5:
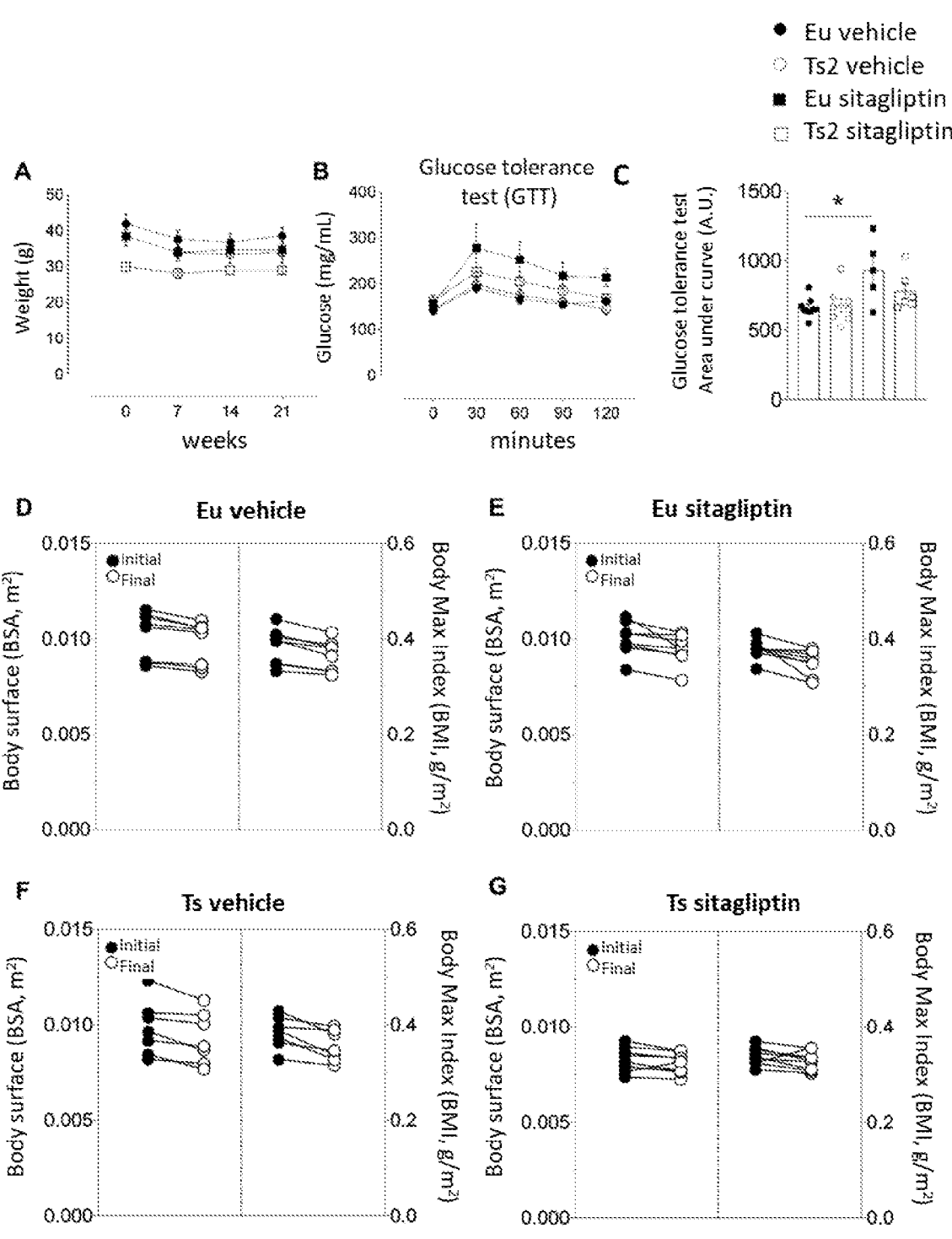
FIG. 5 illustrates the effects of sitagliptin administration on the morphometric characteristics of the animals. In (A), change in weight measured in grams (g) during the course of treatment. In (B) and (C) results of the glucose tolerance test (GTT) carried out at the end of the treatment to evaluate whether the intranasal administration of sitagliptin promotes peripheral effects on the glucose metabolism. The curve in (B) represents plasma glucose concentration measured in mice fasted for 6 hours, at 0, 30, 60, 90 and 120 minutes after intraperitoneal administration of glucose (10% in physiological solution). The histograms in (C) represent the value of the area under the curve. In (D-G), changes in body surface area (BSA) and body mass index (BMI) measured at the beginning (T=0, initial) and at the end (T=21, final) of treatment in mice of each group. *, p<0.05, ANOVA analysis followed by Bonferroni corrected t-test.

At the same time, the treatment regimen was found to be safe as no phenotypic or morphometric changes or changes in glucose metabolism indices were observed in sitagliptin-treated Ts2Cje mice (FIG. 5).

Figure 6:
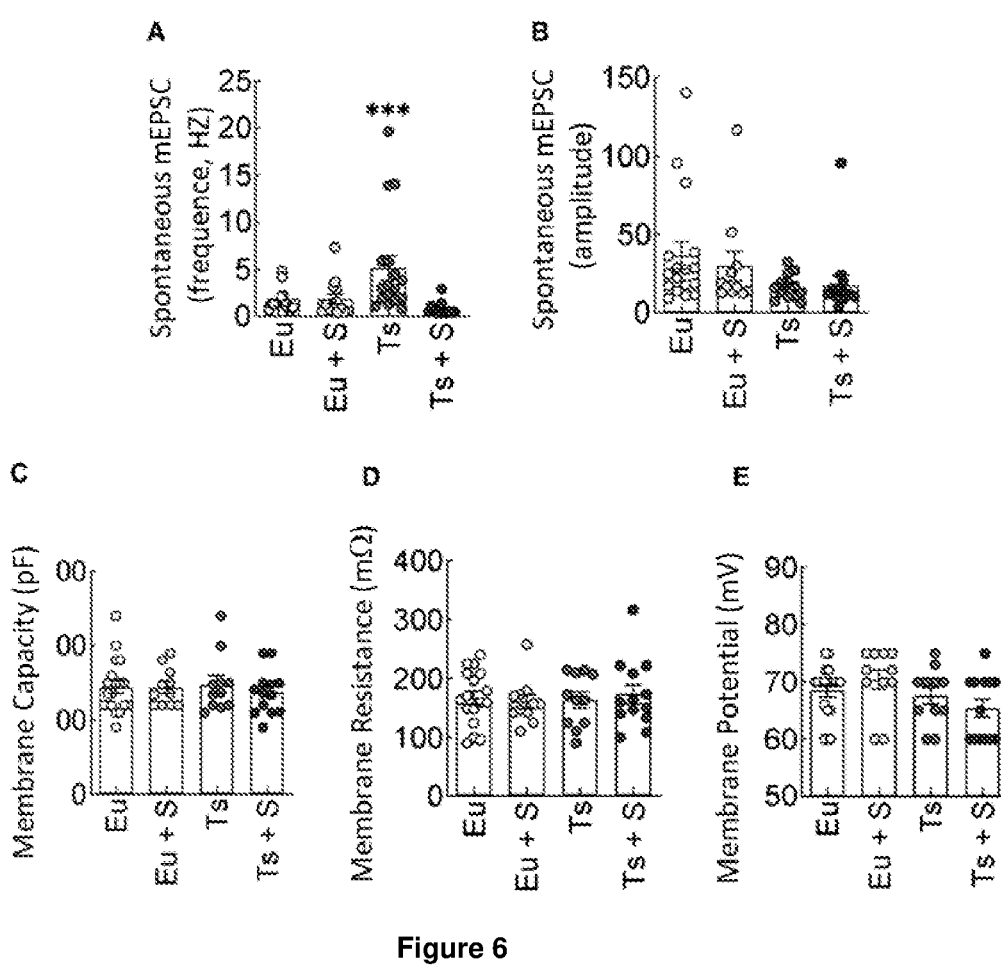
FIG. 6 illustrates the results of electrophysiological analysis conducted at the end of treatment with sitagliptin. mEPSC: excitatory post-synaptic currents; Eu: vehicle-treated euploid mice; Eu+S: euploid mice treated with sitagliptin; Ts: Vehicle-treated Ts2Cje mice; Ts+S: Ts2Cje mice treated with sitagliptin. (*, p<0.05 Ts+S vs Ts ANOVA analysis followed by Bonferroni corrected t test)

The improvement observed in cognitive tests was also supported by results obtained by electrophysiological analysis showing the complete restoration of GABAergic transmission in Ts2Cje mice treated with the composition comprising sitagliptin (FIG. 6). In particular, a significant increase in the spontaneous release rate of the neurotransmitter is observed in Ts2Cje mice compared to Eu mice (A), as demonstrated with patch-clamp experiments in neurons of the CA1 region of the hippocampus. The amplitude of the signals is not significantly different between Ts2Cje and Eu (B) mice, which correlates with a presynaptic and/or generalized effect at the circuit level. Pharmacological treatment of Ts2Cje (Ts+S) mice completely reverts the increase in the spontaneous release rate of the neurotransmitter observed in Ts2Cje mice (A). The composition has no effect on the frequency and extent of spontaneous release of neurotransmitters in Eu mice (A and B). The increase in the spontaneous release frequency of the neurotransmitter is correlated with an increase in hippocampal excitability. The study of membrane capacity (C) and input resistance (D) indicates that the analyzed neurons possess similar biophysical properties. The membrane potential is not significantly different in the various groups studied (E). These data indicate that the increase in excitability observed in Ts mice could be due to an altered activity of GABAergic neurons, and that sitagliptin is able to restore the electrophysiological alterations observed in Ts2Cje mice.

Figure 7:
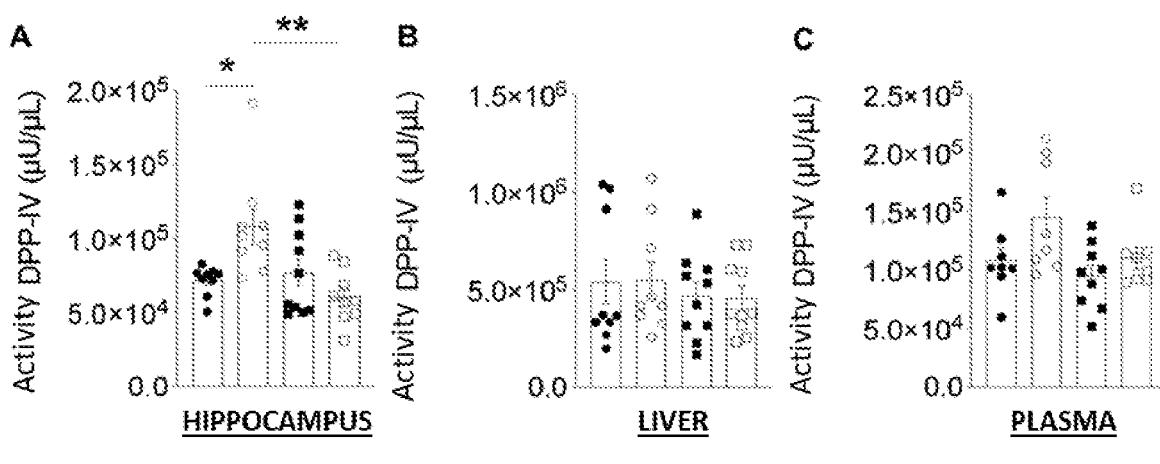
FIG. 7 illustrates the analysis of DPP4 enzyme activity in tissue samples isolated from Euploid and Ts2Cje mice following treatment with sitagliptin. Analysis of DPP4 enzyme activity in hippocampus, liver and plasma samples isolated at the end of treatment with sitagliptin. Eu: euploid mice; Ts: Ts2Cje mice. *, p<0.05 and **p<0.01 ANOVA analysis followed by Bonferroni corrected t-test.

Another relevant aspect of the composition described in this application concerns the evidence that it was found to be able to reduce activation of the DPP4 enzyme at the hippocampal level without promoting significant effects at the peripheral level (FIG. 7). The importance of this aspect is correlated with the fact that the aim of using the composition is to restore the activity of the DPP4 enzyme only and selectively in the areas where a greater activation of this enzyme has been observed, and not in others.

Figure 8:
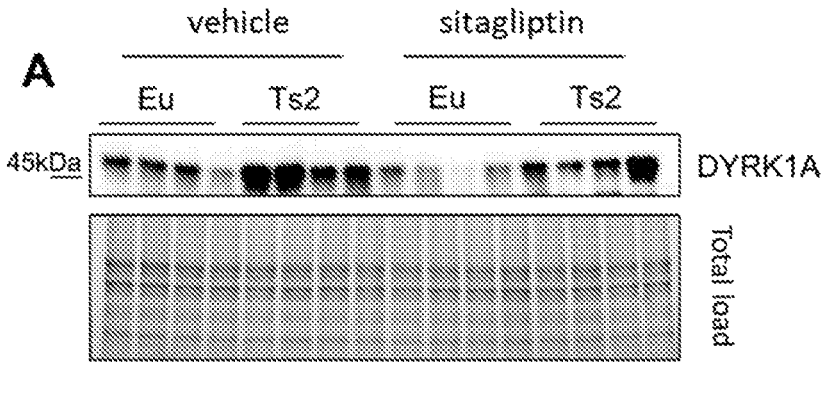
FIG. 8 concerns the effects of sitagliptin administration on the total levels of DYRK1A protein. In (A) Representative image of the Western blot and of the electrophoretic run (gel-normalizer, total proteins) of the DYRK1A protein levels evaluated in the hippocampus of the four experimental groups. In (B) the histograms report the densitometric analysis of DYRK1A levels, respectively in euploid and Ts2Cje animals treated with sitagliptin or vehicle (saline solution). The reported densitometry values are expressed as a percentage of the Eu group treated with the vehicle. Data are presented as means±SEM, *p<0.05, ANOVA analysis followed by Bonferroni corrected t test.
Figure 8:
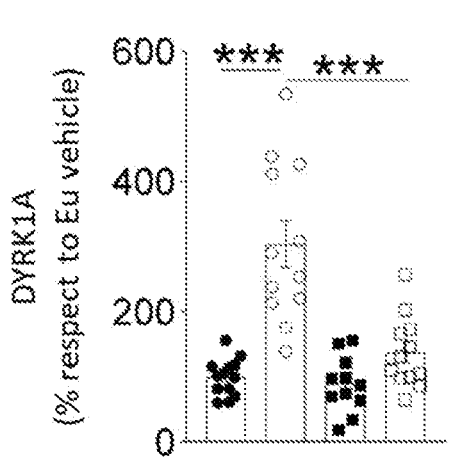

From a molecular point of view, sitagliptin treatment promotes a significant reduction in expression levels of the DYRK1A protein in the hippocampus of Ts2Cje mice (FIG. 8), wherein panel (A) shows a representative image of the Western blot and the electrophoretic run of DYRK1A protein levels evaluated in the hippocampus of four experimental groups; panel (B) shows histograms relative to the densitometric analysis of DYRK1A levels in euploid and Ts2Cje animals treated, respectively, with sitagliptin or vehicle (saline solution).

This result, never observed before, is very encouraging as DYRK1A is one of the proteins encoded at chromosome 21 and, therefore, over-expressed in DS. Furthermore, DYRK1A plays a fundamental role in neuronal development. Transgenic mouse models characterized by the over-expression of DYRK1A (mBACtgDYRK1A mice) show changes in brain size and neuronal density, neurodevelopmental delays, motor abnormalities, impaired synaptic plasticity, learning and memory deficits. Similar characteristics are observed in DS, where over-expression of DYRK1A has been linked to cognitive deficit and to the imbalance existing between the mechanisms that mediate the processes of excitation and inhibition at the neuronal level.

Figure 9:
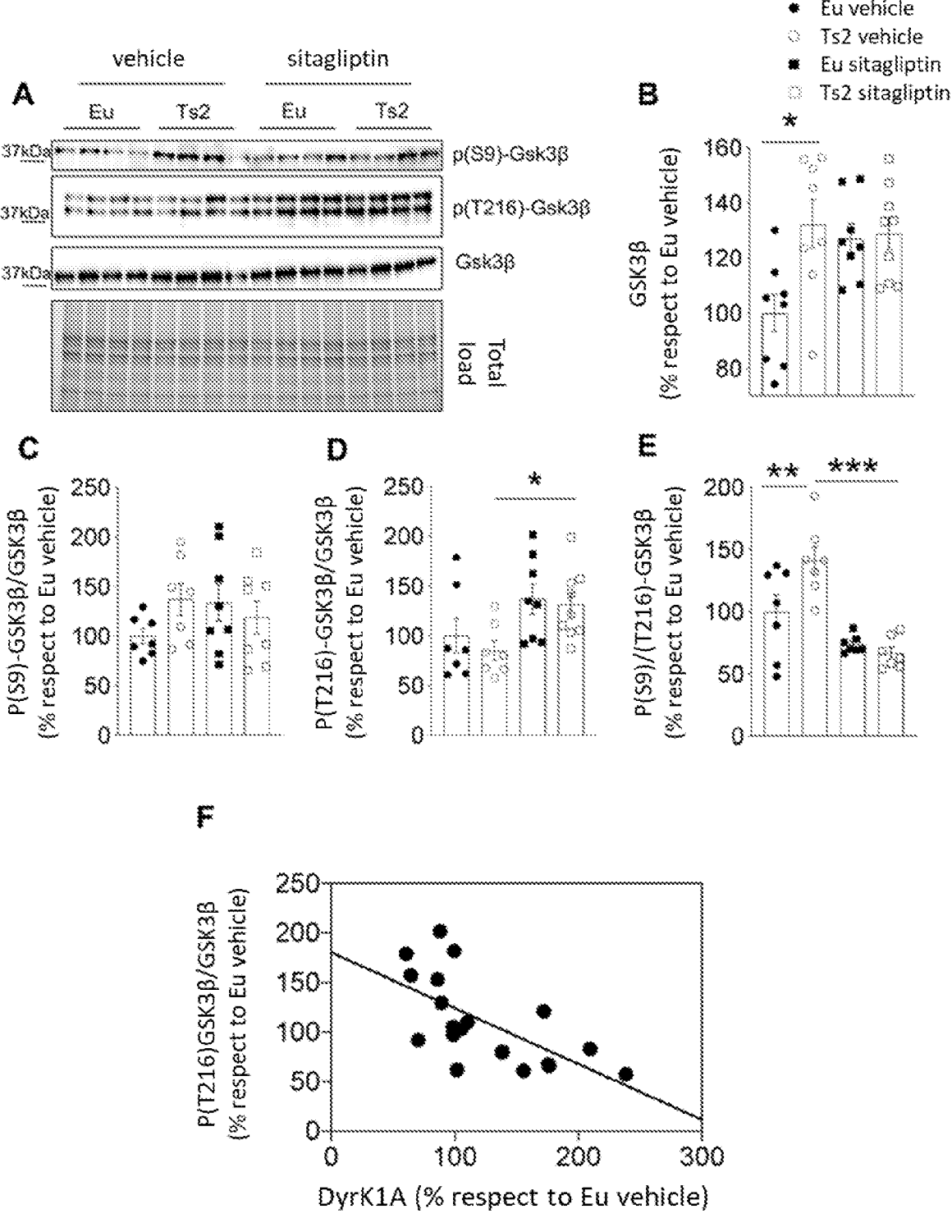
FIG. 9 relates to an evaluation of the administration of sitagliptin on the activation of the GSK3b protein. The reported densitometry values are expressed as a percentage of the Eu group treated with vehicle. Data are presented as means±SEM, *p<0.05, ANOVA analysis followed by Bonferroni corrected t-test. (F) Linear regression performed by evaluating the variations of the active form of GSK3b with respect to the protein levels of DYRK1A in the four experimental groups.

Furthermore, DYRK1A promotes inhibition of the glycogen synthase kinase 3 beta (GSK3b) protein. The Inventors of the instant application show how the reduction in DYRK1A levels mediated by sitagliptin is associated with an increased activation of the GSK3b protein in the brains of Ts2Cje mice. FIG. 9, panel A, shows the results of experimental tests conducted by Western blot and electrophoretic run relating to the levels of GSK3b protein and its phosphorylated forms (inhibited: pS9; active: pT216). The total levels of GSK3b and its inhibition/activation state were measured in the hippocampus of the four experimental groups. The histograms show the densitometric analysis of the total levels of total protein (B), its inhibited form (C) and its active form (D), the latter two normalized with respect to the total protein levels. Furthermore, the graph in (E) shows the overall activation status of GSK3b as the ratio between the inhibited and the active form (pS9/pT216) in euploid and Ts2Cje animals treated, respectively, with sitagliptin or vehicle (saline solution). Panel F indicates the linear regression performed by evaluating the variations of the active form of GSK3b with respect to the protein levels of DYRK1A in the four experimental groups.

The aforesaid experimental evidence proved to be the basis of the innovative aspect of the composition described, as the data available in the literature, on the contrary, suggest that an excessive activation of GSK3b in the brain promotes neurotoxic effects (for example, an increase in the phosphorylation of the Tau protein in the AD). Despite this, it should be emphasized that DS, unlike other neurodegenerative diseases, has peculiar characteristics due to the trisomy of chromosome 21 that make it a fairly unique condition. From this perspective, over-expression of DYRK1A would promote a persistent inhibition of GSK3b, and this alteration would be at the basis of the defects in GABAergic transmission.

Figure 10:
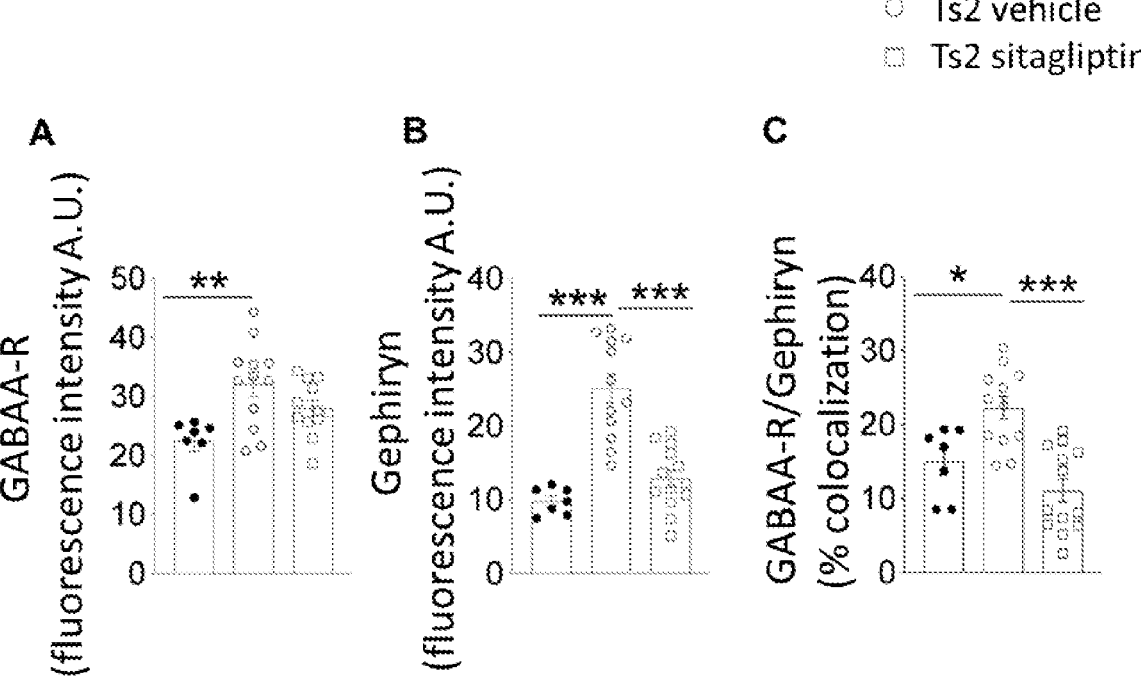
FIG. 10 relates to an evaluation of the administration of sitagliptin on the co-localization of the GABAA receptor (GABAA-R) and of the gephyrin protein. Histograms show immunofluorescence analysis in hippocampal regions CA3 and CA1 of euploid mice treated with vehicle and Ts2Cje treated with sitagliptin or vehicle (saline solution) for evaluating GABAA-R (A) and gephyrin (B) protein expression. The graph in (C) reports the analysis to estimate the effects of sitagliptin on the co-localization between GABAA-R and gephyrin protein in CA3 and CA1 in euploid and Ts2Cje mice treated with sitagliptin or vehicle. The histograms show the fluorescence intensity (MFI). Data are presented as means±SEM, * p<0.05, ANOVA analysis followed by Bonferroni corrected t test.

The GSK3b protein, in addition to being involved in the insulin signaling pathway, promotes phosphorylation and consequent degradation of the gephyrin protein, which regulates the turnover of GABAA receptors at synapse level (FIG. 1). The results obtained by the Inventors of the present application clearly show that activation of the GSK3b protein following intranasal treatment with the composition is associated with a reduction of the clusters of gephyrin and GABAA-R at the synaptic level (evaluated through confocal microscopy) (FIG. 10), and this evidence also explains the restoration of GABAergic transmission observed in the electrophysiology studies described above (FIG. 6).

Figure 11:
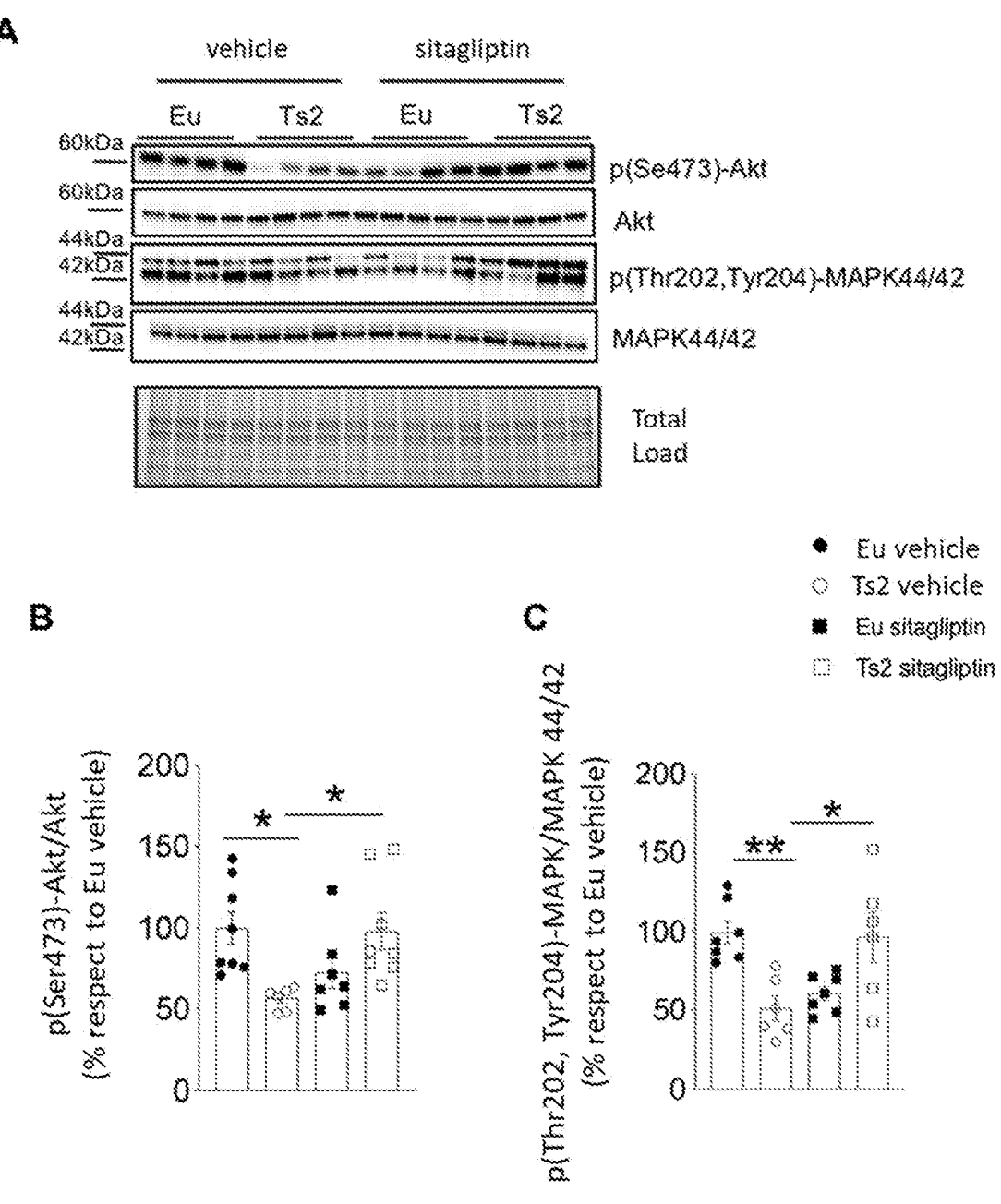
FIG. 11 shows the effects of sitagliptin administration on the activation of Akt and MAPK44/42 proteins in the hippocampus of Eu and Ts2Cje mice. In (A) representative images of the Western blot and of the electrophoretic run (gel-normalizer, total proteins) of the phosphorylation levels and of the total levels of the following proteins: p(ser473)-Akt, Akt, p(Thr202, Tyr204)-MAPK44/42 and MAPK44/42. In (B) densitometric analysis relating to the activation of the Akt protein and in (C) densitometric analysis relating to MAPK44/42 activation, respectively, in euploid and Ts2Cje animals treated with sitagliptin or vehicle (saline solution). The reported densitometry values are expressed as a percentage of the Eu group treated with the vehicle. Data are presented as means±SEM, * p<0.05, ANOVA analysis followed by Bonferroni corrected t test.
Figure 12:
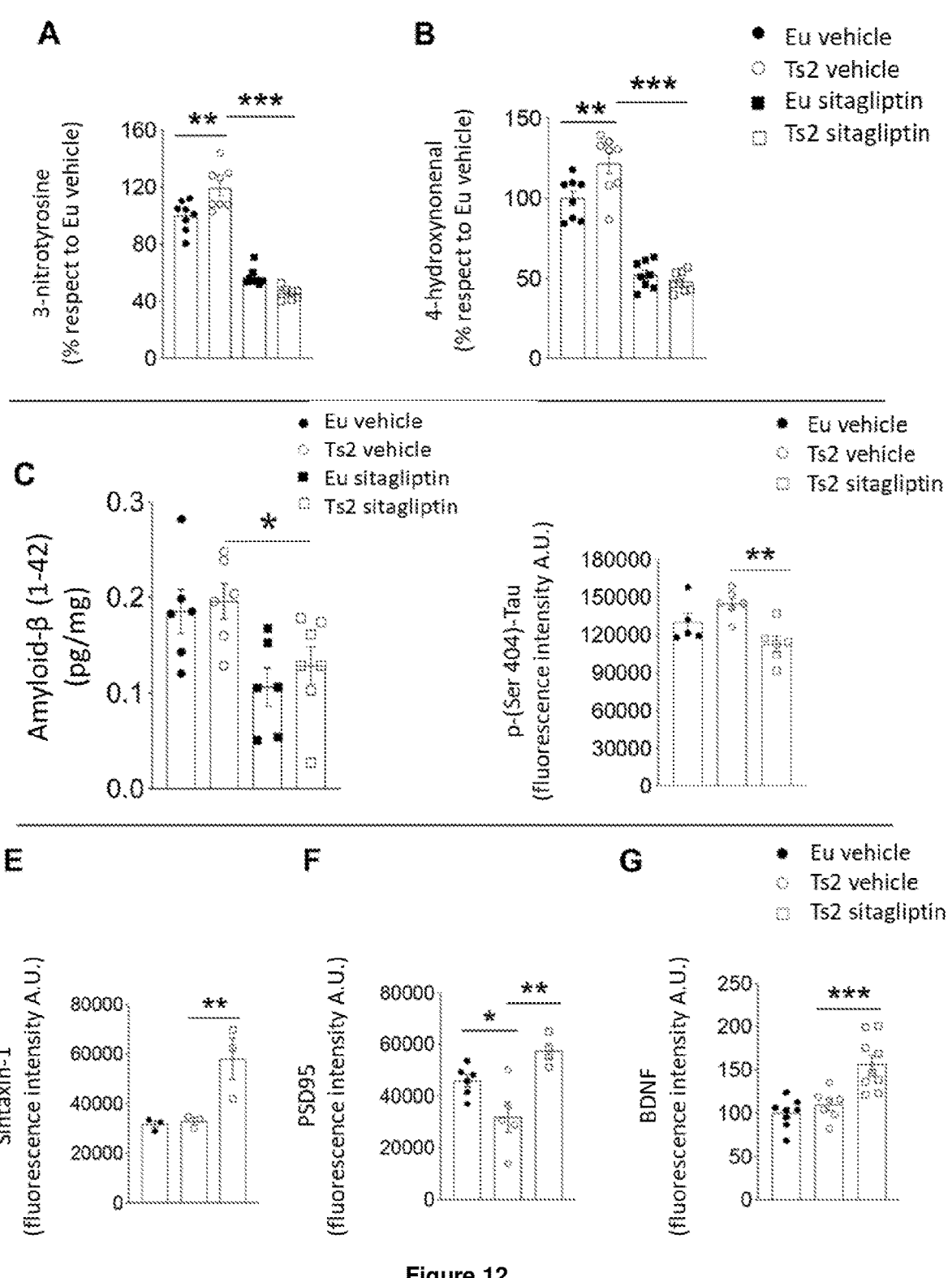
FIG. 12 shows the effects of sitagliptin administration on oxidative stress levels (A-B), on beta-amyloid (Ab) and phosphorylated Tau (pTau Ser404) (C-D) levels, and on the levels of proteins normally associated with synaptic plasticity such as sintaxin-1, post-synaptic density protein 95 (PSD95) and brain-derived neurotrophic factor (BDNF) (E-G) protein in the hippocampus of euploid and Ts2Cje mice. Oxidative stress levels were detected by measuring two of the main post-transductional modifications of lipid and protein oxidation using the slot blot technique: (A) 3-nitrotyrosine (3-NT, following nitration of tyrosine residues) and (B) 4-hydroxynonenal (4-HNE, product of lipid peroxidation). The reported densitometry values are expressed as a percentage of the Eu group treated with vehicle. The quantitative evaluation of AB 1-42 (C) and phosphorylated tau on Ser404 (D) outlines the effects of sitagliptin administration on the neuropathological aspects of Alzheimer's. The quantitative determination of AB 1-42 took place through the use of an ELISA kit. Phosphorylation levels of Tau on Ser 404 were measured by immunofluorescence. The levels of three proteins involved in synaptic transmission were measured by immunofluorescence. The graphs report the fluorescence intensity for sintaxin-1, a presynaptic marker (E), PSD95, a postsynaptic marker (F) and BDNF, a neuronal growth factor (G). Data are presented as means±SEM, * p<0.05, ANOVA analysis followed by Bonferroni corrected t test.

The DPP4/DYRK1A/GSK3b/gephyrin/GABAA-R axis, therefore, represents a molecular mechanism for the first time identified by the Inventors of this application (FIG. 1), a molecular mechanism through which the neuroprotective effects of the composition comprising sitagliptin are expressed in DS. Furthermore, following administration of the composition, the following results were observed: i) restoration of the activation of the cerebral insulin signal at the level of the MAPK44/42 and Akt pathway (FIG. 11), known to mediate neuroprotective effects; ii) a reduction in oxidative stress levels, Ab and phosphorylated Tau (FIG. 12A-D), iii) an increase in the proteins involved in synaptic transmission (sintaxin-1, PSD95 and BDNF) (FIG. 12E-G).

Figure 13:
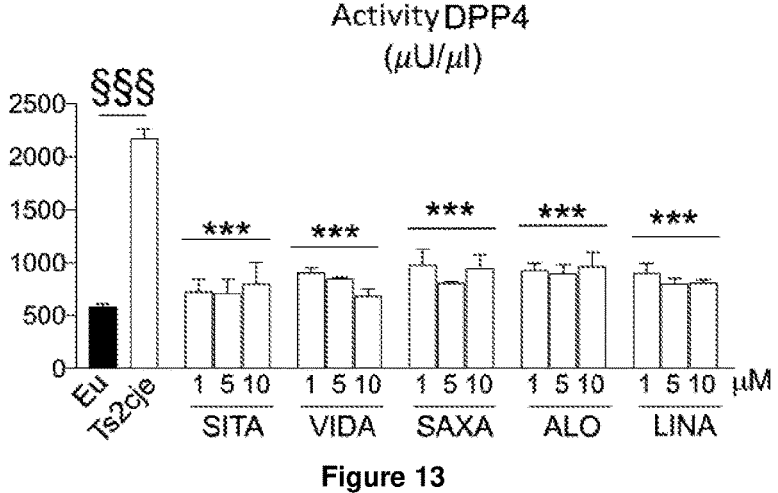
FIG. 13 shows the analysis of the DPP4 enzyme activity in response to treatment with gliptins tested on hippocampal neurons isolated from Ts2cje mice. Neurons were isolated from the hippocampus of Euploid (Eu) and Ts2cje mice, the Ts2cje mice were treated with five different gliptins: Sitagliptin (SITA), Vidagliptin (VIDA), Saxagliptin (SAXA), Alogliptin (ALO) and Linagliptin (LINA), using three different doses (1 μM, 5 μM, 10 μM) for 24 hours. § § §

The efficacy of a series of compounds belonging to the class of gliptins has also been demonstrated on a line of primary neurons isolated from euploid (Eu) mice and Ts2Cje mice. As can be seen from the results illustrated in FIGS. 13-15, the primary hippocampal neurons isolated from the Ts2Cje mouse are characterized by increased activity of the DPP4 enzyme (FIG. 13), which is associated with the over-expression of the DYRK1A protein (FIG. 14), and greater inhibition of the GSK3B protein (identified by the pSer9/pTyr216 ratio, FIG. 15), compared to hippocampal neurons isolated from Eu mice.

These results are comparable to those obtained in vivo following analysis of hippocampal samples isolated from Eu and Ts2Cje mice, and support the choice of using primary neurons as an experimental model to test the effects of other compounds belonging to the class of gliptins. Sitagliptin, vildagliptin, saxagliptin, linagliptin, and alogliptin administered to primary cultures of primary hippocampal neurons isolated from Ts2Cje mice resulted in significant inhibition of the activity of the DPP4 enzyme in Ts2Cje neurons (FIG. 13), ii) a significant reduction in levels of the DYRK1A protein (FIG. 14), and iii) a significant increase in the activity of the GSK3B protein (FIG. 15). These results, which perfectly match the results obtained following the administration of sitagliptin in vivo in Ts2 Cje mice, support the efficacy and possibility of using compounds belonging to the class of gliptins in preventing and/or treating intellectual disabilities and neurodegenerative diseases in a subject with Down syndrome.

The invention claimed is:

1. A method of treatment of intellectual disability and neurodegenerative diseases in a subject with Down syndrome, comprising administering a composition comprising as active agent at least one compound belonging to the class of dipeptidyl-peptidase IV (DPP4) enzyme inhibitors and also to the class of gliptins.

2. The method according to claim 1, wherein said at least one compound belonging to the class of DPP4 inhibitors and to the class of gliptins is selected from the group consisting of sitagliptin, vildagliptin, saxagliptin, linagliptin, gemigliptin, anagliptin, tenegliptin, alogliptin, trelagliptin, omarigliptin, evogliptin, glosogliptin, and dutogliptin.

3. The method according to claim 1, wherein said at least one compound belonging to the class of DPP4 inhibitors and to the class of gliptins is sitagliptin.

4. The method according to claim 1, wherein said neurodegenerative diseases comprise Alzheimer's disease.

5. The method according to claim 1, wherein said at least one compound belonging to the class of DPP4 inhibitors and to the class of gliptins is contained in the composition in a concentration comprised between 0.1 mM and 50 mM.

6. The method according to claim 1, wherein the composition is an intranasal composition.

7. The method according to claim 1, wherein the composition comprises at least one pharmaceutically acceptable vehicle.

8. The method according to claim 5, wherein said at least one compound belonging to the class of DPP4 inhibitors and to the class of gliptins is contained in the composition in a concentration comprised between 0.5 mM and 2.5 mM.

9. The method according to claim 7, wherein the pharmaceutically acceptable vehicle is selected from the group consisting of buffer solutions, physiological saline solution, and water.

* * * * *